(12) United States Patent
Miyashita et al.

(10) Patent No.: US 6,934,967 B2
(45) Date of Patent: Aug. 30, 2005

(54) WELDING OPERATION LIQUID CRYSTAL PROTECTION MASK

(75) Inventors: Kiyoshi Miyashita, Tokyo (JP); Shunsuke Suyama, Kanagawa (JP)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/381,564

(22) PCT Filed: Nov. 8, 2001

(86) PCT No.: PCT/US01/46495
§ 371 (c)(1),
(2), (4) Date: Mar. 27, 2003

(87) PCT Pub. No.: WO02/38095
PCT Pub. Date: May 16, 2002

(65) Prior Publication Data
US 2004/0031903 A1 Feb. 19, 2004

(30) Foreign Application Priority Data
Nov. 9, 2000 (JP) ..................... 2000-342324

(51) Int. Cl.⁷ ................................. A61F 9/06
(52) U.S. Cl. ............................................. 2/8
(58) Field of Search .................... 2/8, 432; 349/14, 349/116; 250/201.1; 219/147

(56) References Cited

U.S. PATENT DOCUMENTS

| | | | | |
|---|---|---|---|---|
| 4,039,803 A | * | 8/1977 | Harsch ........................ 219/147 |
| 4,071,912 A | * | 2/1978 | Budmiger ........................... 2/8 |
| 4,130,903 A | * | 12/1978 | VAN DEN Berg et al. ......... 2/8 |
| 4,155,122 A | | 5/1979 | Budmiger |
| 4,491,390 A | * | 1/1985 | Tong-Shen .................. 349/116 |
| 4,560,239 A | * | 12/1985 | Katz ........................... 349/14 |
| 4,620,322 A | * | 11/1986 | Eggenschwiler et al. .......... 2/8 |
| 4,920,257 A | | 4/1990 | Fuerthbauer et al. |
| 5,302,815 A | * | 4/1994 | Eggenschwiler ......... 250/201.1 |
| 5,377,032 A | * | 12/1994 | Fergason et al. .............. 349/14 |
| 5,510,609 A | | 4/1996 | Ackermann |
| 5,515,186 A | * | 5/1996 | Fergason et al. .............. 349/14 |
| 5,533,206 A | * | 7/1996 | Petrie et al. ...................... 2/8 |
| 5,854,667 A | * | 12/1998 | Ackermann ................. 349/187 |
| 6,021,520 A | * | 2/2000 | Wang-Lee ........................ 2/8 |
| 6,270,223 B1 | * | 8/2001 | Del Bon et al. ............ 359/601 |

FOREIGN PATENT DOCUMENTS

| | | |
|---|---|---|
| EP | 0678288 | 10/1995 |
| GB | 1430183 | 3/1976 |
| WO | WO 96/10767 | 4/1996 |

OTHER PUBLICATIONS

Patent Abstracts of Japan, vol. 015, No. 205 (p 1206) (May 27, 1991) and JP 03 054521 (Mar. 8, 1991).

* cited by examiner

*Primary Examiner*—Rodney M. Lindsey
(74) *Attorney, Agent, or Firm*—Karl G. Hanson

(57) ABSTRACT

A welding-operation, liquid crystal, protection mask for protecting the eyes of a human operator from an arc light generated during a welding operation, comprises a liquid crystal protection mask main body adapted to be attached to the face of a human operator; a detecting means disposed in the vicinity of the liquid crystal protection mask main body and capable of detecting an incident arc light generated during the welding operation and thus producing a detection result; a liquid crystal light blocking section that is disposed in a position corresponding to the eyes of a human operator wearing the protection mask with the human face being covered by the protection mask main body and that has a liquid crystal member that is capable of blocking the incident light by instantaneously reducing the light transmittance of the liquid crystal in accordance with the detection result output from the detecting means and by means of a liquid crystal driving power source; and a polarizing plate that is provided in front of the detecting means to cover up the detecting means and that is capable of controlling the orientation of the incident light.

12 Claims, 1 Drawing Sheet

WELDING OPERATION LIQUID CRYSTAL PROTECTION MASK

The present invention relates to a welding-operation, liquid crystal, protection mask that has a light blocking device for protecting the eyes of a human operator from an arc light generated during a welding operation. In more detail, the present invention relates to a welding-operation, liquid crystal, protection mask that is simple in structure but excellent in its detection precision when detecting an arc light, so that the light blocking device will actuate only when a human operator who wears the liquid crystal protection mask has their arc light on. The invention thus prevents a welding mask from improperly operating when it detects light(s) other than the arc light of the operator, thereby improving operator's safety during a welding operation.

BACKGROUND

In the past, a light protection mask has used a light blocking plate to protect a human operator's eyes from an arc light that is generated during a welding operation. More recently, a welding-operation, liquid crystal, protection mask has been developed, which mask is equipped with a liquid crystal plate that is capable of blocking a light by instantaneously reducing the light transmittance of a liquid crystal. These known welding-operation, liquid crystal, protection masks, however, have been found to have some drawbacks. When many human operators are conducting welding operations at the same time, the light transmittance of the light blocking plate being used by one human operator may be undesirably actuated by nearby arc lights of other welders and also by illumination lights.

Because known welding-operation, liquid crystal, protection masks are designed for the purpose of sufficiently protecting the eyes of a human operator, they are usually constructed so that light transmittance during a light blocking operation is extremely small. As a result, a human operator typically can recognize nothing but a welding point when the device is activated. For this reason, when a mistaken light blocking operation occurs that is out of control of a human operator during the welding operation, the operator will suddenly become unable to see, creating an extremely dangerous condition for them.

In order to prevent this situation from occurring, it has been suggested that a light blocking cylindrical member be used in front of a light receiving member, which cylindrical member consists of an ultraviolet light detecting element, so as to form an improved welding-operation, liquid crystal, protection mask that only responds to incident light that arrives from the front (see Japanese Unexamined Patent Application Publication No. 2-159272). This known welding-operation, liquid crystal, protection mask is beneficial in that it can treat an arc light entering at an incidence angle of a certain narrow range from a position ahead of the light receiving member.

The arc light detector, however, not only responds to an arc light entering at an incidence angle of a narrow range from a position ahead of the light receiving member, but also responds to other lights that reach the light receiving member from other directions, including arc lights generated and reflected during the welding operations of other human operators. As a result, the cylindrical light blocking member used in the above-discussed liquid crystal protection mask fails to effectively avoid a problem of detecting other lights. Thus, it has been proved difficult to obtain a desired and satisfactory detection precision.

SUMMARY OF THE INVENTION

The present invention is provided to overcome the above problems by furnishing the art with an improved welding-operation, liquid crystal, protection mask that has a light blocking device for protecting the eyes of a human operator from an arc light generated during a welding operation. Specifically, the present invention provides a welding-operation, liquid crystal, protection mask that is simple in structure but excellent in its detection precision when detecting an arc light, so that the light blocking device will actuate only when the liquid crystal protection mask has detected an arc light of that user during their welding operation, thus preventing a mistaken light blocking operation, which is possibly caused by the light blocking device when it has detected a non-arc light. The invention thus has the benefit of improving the safety of the human operator during a welding operation.

According to the present invention, there is provided a welding-operation, liquid crystal, protection mask for protecting the eyes of a human operator from an arc light generated during a welding operation, which comprises a liquid crystal protection mask main body that is adapted to be attached to the face of a human operator; a detecting means disposed in the vicinity of the liquid crystal protection mask main body and capable of detecting an incident arc light generated during the welding operation and thus producing a detection result; a liquid crystal light blocking section that is disposed in a position corresponding to the eyes of a human operator wearing the protection mask with the human face being covered by the protection mask main body, and which has a liquid crystal member capable of blocking the incident light by instantaneously reducing the light transmittance of the liquid crystal in accordance with the detection result output from the detecting means and by means of a liquid crystal driving power source; and a polarizing member that is provided in front of the detecting means to cover up the detecting means, and which is capable of controlling the orientation of the incident light.

The welding-operation, liquid crystal, protection mask may further comprise a cover plate that is disposed so as to cover up at least the front surface of the liquid crystal light blocking section, to protect the liquid crystal member from welding sputters and a mechanical stress during the welding operation.

In the welding-operation, liquid crystal, protection mask, the polarizing member may be a polarizing film that is formed by two pieces of plastic films that have a louver device interposed therebetween.

In the welding-operation, liquid crystal, protection mask, the polarizing member may be constructed that when lights are incident on the polarizing member, only the lights having incidence angles of 24 degrees or smaller (right and left with respect to the rectilinearly propagating light) are allowed to pass through the polarizing member, thereby effecting the control of the orientation of the incident arc light. The detecting means may also include an open-ended cylindrical member disposed in a predetermined position adjacent to the liquid crystal light blocking section, and a light receiving member disposed on the bottom of the open-ended cylindrical member for receiving an incident light.

The liquid crystal member may be a liquid crystal plate, the liquid crystal driving power source may be a solar battery, and the cover plate may be a transparent protection plate.

The present invention can provide a welding-operation, liquid crystal, protection mask that is simple in structure but excellent in its detecting precision when detecting an arc light, so that the light blocking device will actuate only when a human operator wearing the liquid crystal protection mask has detected an arc light during his or her welding operation, thus preventing a mistaken light blocking operation which is often caused by the light blocking device when it has detected a non-arc light, thereby ensuring an improved safety for the human operator in his or her welding operation.

DETAILED DESCRIPTION OF PREFERRED EMBODIMENTS

Figure 1:
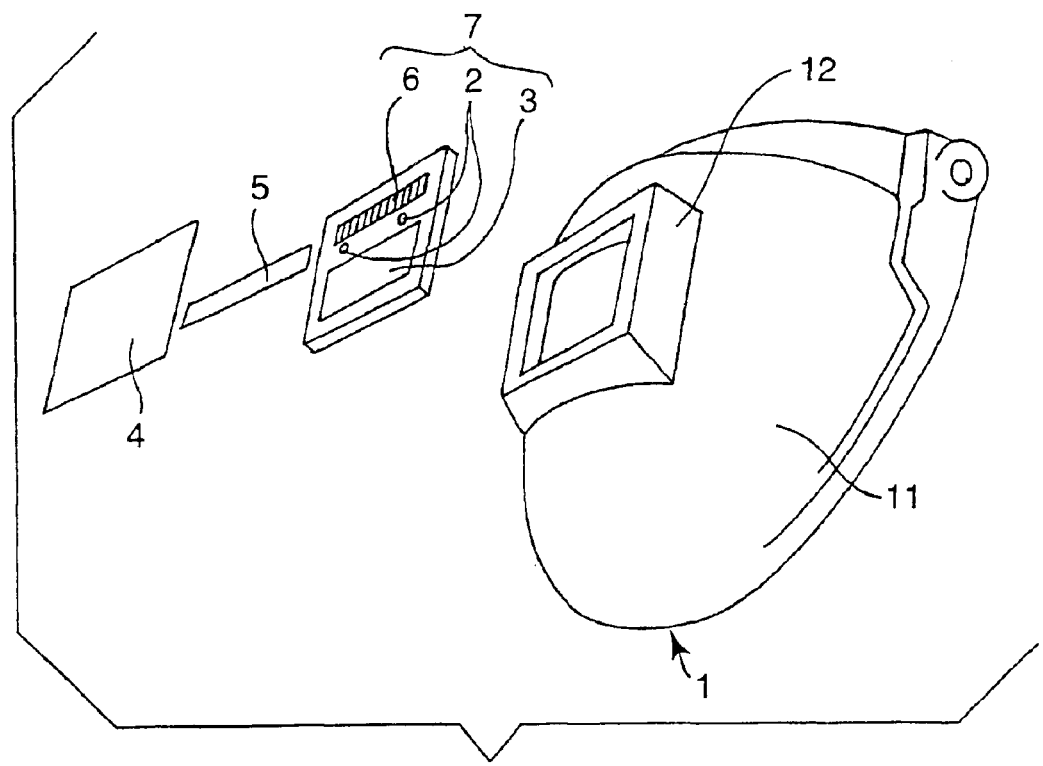
FIG. 1 is a perspective view that schematically shows an embodiment of a welding-operation, liquid crystal, protection mask according to the present invention.

As shown in FIG. 1, a welding-operation, liquid crystal, protection mask of the present invention is a protection mask for protecting the eyes of a human operator from an arc light generated during his or her welding operation. Specifically, the welding-operation, liquid crystal, protection mask is characterized in that it comprises a liquid crystal protection mask main body 1 that is adapted to be attached to the face of a human operator; a detecting means 2 disposed in the vicinity of the liquid crystal protection mask main body 1 and capable of detecting an incident arc light generated during the welding operation and thus producing a detection result; a liquid crystal light blocking section 3 that is disposed in a position corresponding to the eyes of a human operator wearing the protection mask with his or her face being covered by the protection mask main body 1 and that has a liquid crystal member that is capable of blocking the incident light by instantaneously reducing the light transmittance of the liquid crystal in accordance with the detection result output from the detecting means 2; a cover plate 4 that (if used) is disposed in front of the liquid crystal light blocking section 3 so as to protect the liquid crystal member and the like from sputters during the welding operation. The welding-operation, liquid crystal, protection mask may further have a polarizing member 5 that is capable of controlling the orientation of the incident light and that is provided in front of the detecting means 2 so as to cover up the detecting means.

Each of the above elements forming the welding-operation, liquid crystal, protection mask are further described in detail below.

1. Liquid Crystal Protection Mask Main Body

In order to protect a human operator from harmful welding sputters and to protect the eyes of the human operator from an arc light by means of the liquid crystal blocking section (that will be described later), the liquid crystal protection mask main body of the present invention is preferred to be made from a specific material and is preferred to have a specific shape such that it can be easily fit on the face of a human operator and can enable the human operator to clearly recognize a welding position after they have donned the protection mask. For example, the protection mask main body may be made from either a metal such as a steel or a plastic material such as a polycarbonate, which has an excellent flame resistance, heat resistance, and abrasion resistance, and should have an appropriate shape suitable for covering the entire face of a human operator after the human operator has put it on.

The detailed structure of the liquid crystal protection mask main body is shown in FIG. 1. As illustrated in the drawing, the protection mask main body includes a human face contact portion 11 and an engaging section 12, the latter of which is adapted to receive a liquid crystal unit 7 that contains the detecting means 2, the liquid crystal light blocking section 3, and a liquid crystal driving power source 6.

The liquid crystal protection mask main body may also be attached, for example, to a helmet or a band, so that it can be fixed on the head of a human operator when it is being used.

2. Liquid Crystal Light Blocking Section

The liquid crystal light blocking section of the present invention may be disposed in a position corresponding to the eyes of a human operator who wears the protection mask with their face being covered by the protection mask main body, so as to effectively block an arc light generated during the welding operation.

The liquid crystal light blocking section of the present invention may have a liquid crystal member that is capable of detecting, by virtue of the detecting means (which will be described in more detail below), an arc light generated during the welding operation, and then instantaneously reducing the light transmittance of the liquid crystal by means of a liquid crystal driving power source, thereby blocking an incident arc light.

For use as such a liquid crystal member, it is preferred to use one that is capable of changing the light transmittance thereof continuously or in a plurality of steps, in accordance with the magnitude of a voltage being applied thereon.

As a preferred example for use as the liquid crystal member, it is allowed to give out the following liquid crystal plate.

For example, it is possible to use a liquid crystal plate that is formed by laminating together two liquid crystal films, capable of changing the light transmittance of an entire liquid crystal in a plurality of steps by changing the light transmittance of the individual liquid crystal films. Alternatively, a variable resistor is connected between the detecting means and the liquid crystal light blocking section so as to adjust an applied voltage.

As shown in FIG. 1, the liquid crystal light blocking section 3, the detecting means 2 and the liquid crystal driving power source 6, are arranged in a manner such that a liquid crystal unit 7 is integrally formed from these elements. The liquid crystal unit 7 is then engaged into the engaging section 12 formed on the main body 1 of the liquid crystal protection mask.

For use as the liquid crystal driving power source, it is preferred to use a solar battery that is small in thickness and light in weight, and is capable of converting lights in the surrounding environment and an arc light generated during a welding operation into an electric energy.

In addition, such a liquid crystal driving power source can also be used to drive the detecting means, as will be described in the following.

3. Detecting Means

As shown in FIG. 1, the detecting means 2 of the present invention may be disposed in a predetermined position adjacent to both the liquid crystal protection mask main body 1 and the liquid crystal light blocking section 3, so as to detect the incident arc light generated during the welding operation and to produce a detection result to the liquid crystal light blocking section 3.

Figure 2:
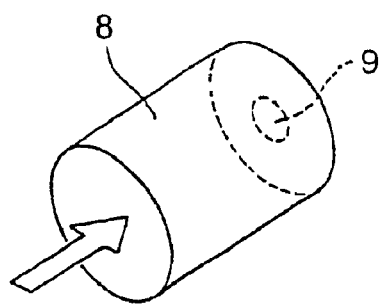
FIG. 2 is a perspective view that schematically shows a detecting means used in the embodiment of the welding-operation, liquid crystal, protection mask according to the present invention.

As a preferred example of the detecting means, FIG. 2 shows a cylindrical member 8 that has both ends thereof opened and disposed in a predetermined position adjacent to the liquid crystal light blocking section 3. FIG. 2 also includes a light receiving member 9 disposed on the bottom of the open-ended cylindrical member 8 for receiving an incident light.

As the open-ended cylindrical member, it is allowed to use a structure either having an elliptical cross section with its longer axis being about 5 mm and its shorter axis being about 3 mm, or having a circular cross section with its diameter being about 4 mm. In both cases, the open-ended cylindrical member has a depth of about 7 mm.

As the light receiving member that is disposed on the bottom of the open-ended cylindrical member, it is allowed to use a structure that has a detecting means capable of detecting an ultraviolet light, a visible light, and an infrared light, and which is so constructed that a signal will be input into the liquid crystal light blocking section when a predetermined amount of light has been incident on the detecting means.

4. Cover Plate

The cover plate which (if used) is disposed in a manner such that it can cover up at least the front face of the liquid crystal light blocking section, so as to protect the liquid crystal light blocking section from welding sputter and other mechanical stress.

As shown in FIG. 1, the cover plate 4 is disposed so as to cover the entire face of the liquid crystal unit 7 (including the detecting means 2, the liquid crystal light blocking section 3, and the liquid crystal driving power source (solar battery 6)).

There is not any specific restriction to the cover plate, provided that it has a desired light transmittancy. For example, the cover plate may take the form of an inorganic plate such as a glass plate and a ceramic plate, or a plastic plate such as a polycarbonate plate and an acryl plate each having an excellent flame resistance, heat resistance and abrasion resistance.

The cover plate, for example, may be engaged into a cover plate engaging section (not shown) provided on the liquid crystal unit.

5. Polarizing Member

As shown in FIG. 1, the polarizing member 5 that can be used in the present invention is shown in front of the detecting means 2 so as to cover the detecting means 2, thereby controlling the orientation of an incident light incident on the detecting means 2.

There is not any limitation to such a polarizing member, provided that it can effectively control the orientation of the incident light. For example, it is preferred to use a polarizing film formed by two pieces of plastic films with a louver device clamped therebetween.

In more detail, the polarizing member may be a plastic film that is equipped with a louver, as disclosed in Japanese Examined Patent Application Publication No. 8-11211 (corresponds to U.S. Pat. No. 4,766,023) and Japanese Unexamined Utility Model Application Publication No. 2-117585. Also, it is possible to use other types of polarizing films such as those that are commercially available under trade names "COMPUTER FILTER PF13B" and "LIGHT CONTROL FILM" and produced by SUMITOMO 3M CO., LTD.

Further, if it is desired to achieve a better detection precision, it is preferred to use a polarizing member that is so constructed such that when lights are incident on the polarizing member, only the lights having incidence angles of 24 degrees or smaller (right and left with respect to the rectilinearly propagating light) are allowed to pass through the polarizing member, thereby effecting the desired control of the orientation of an incident arc light.

The polarizing member may be attached to the mask main body using an adhesive agent, in a manner such that it can cover the upper surface of the detecting means. Alternatively, the polarizing member may be engaged in the cover plate engaging section in which the cover plate is engaged.

Since the polarizing member is light in weight and does not include any protruding portions, it will not hamper a welding operation that is performed by a human operator who wears a protection mask that contains such a polarizing member. In addition, since the use of the polarizing member can provide good detection precision, it is sure for a human operator to perform the welding operation smoothly and with an increased safety.

EXAMPLE

In the following, the present invention will be described in more detail with reference to an example. However, this invention should not be limited to the product so described.

Example 1

A cover plate installed in a liquid crystal type protection mask (commercially available under a trade name "R-SERIESE DM9 LIQUID CRYSTAL TYPE" and produced by Minnesota Mining and Manufacturing Company (3M), U.S.A) was removed from the cover plate engaging section. Then, a polarizing film (commercially available under a trade name "COMPUTER FILTER PF13B" and produced by SUMITOMO 3M CO., LTD.) was engaged into the liquid crystal unit engaging section to cover the front face of the light receiving member of the detecting means. In detail, the polarizing film was in a rectangular shape having a length of 107 mm and a width of 7 mm, and was attached with its longitudinal direction being perpendicular to the arrangement direction of a micro louver. Subsequently, the cover plate was again attached to the liquid crystal unit engaging section and was fixed thereon.

Comparative Example 1

The Comparative Example was carried out in the same manner as the above Example 1, except that the polarizing film was not used.

Evaluation on Detection Precision

Lamps (commercially available under a trade name "PHOTO REFLECTOR LAMP DAYLIGHT COLOR 100 V, 350 W" and produced by LAMP TOSHIBA CO., LTD.) were placed at a distance of 55 cm right above the welding-operation, liquid crystal, protection masks obtained in Example 1 and Comparative Example 1. Then, the lamps were gradually moved away from the above positions while continuously maintaining the above distance. In this way, the incidence angles of the lights from the lamps when they are incident on the detecting means (light receiving members) of the liquid crystal protection masks were changed gradually. At the same time, various incidence angles detected by the detecting means were recorded so that the detection precisions were evaluated.

As a result, it was found that when the protection mask obtained in Example 1 was used, the detecting means could no longer continue its detecting function once the incidence angle became larger than 24 degrees on each side (48 degrees in all) with respect to a rectilinearly propagating light coming from an overhead position right above it. On the other hand, when the protection mask obtained in Comparative Example 1 was used, the detecting means could continue its detecting function until the incidence angle became 35 degrees on each side (70 degrees in all) with respect to a rectilinearly propagating light coming from an overhead position right above it.

What is claimed is:

1. A welding-operation, liquid crystal, protection mask for protecting the eyes of a human operator from an arc light generated during a welding operation, which mask comprises:
   a liquid crystal protection mask main body that is adapted to be attached to the face of a human operator;
   a detecting means that is disposed in the vicinity of the liquid crystal protection mask main body and that is capable of detecting an incident arc light generated during the welding operation and thus producing a detection result;
   a liquid crystal light blocking section that is disposed in a position corresponding to the eyes of a human operator wearing the protection mask with the human face being covered by the protection mask main body and that has a liquid crystal member that is capable of blocking the incident light by instantaneously reducing the light transmittance of the liquid crystal in accordance with the detection result output from the detecting means and by means of a liquid crystal driving power source; and
   a polarizing member that permits light transmittance therethrough when light is incident on the polarizing member in a direction normal thereto to allow the detecting means to produce a detection result but that blocks the transmittance of light sufficiently to not cause the detecting means to produce a detection result when the light is incident thereon at a certain angle exceeding the normal angle of incidence.

2. The welding-operation, liquid crystal, protection mask of claim 1, further comprising:
   a cover plate that is disposed so as to cover up at least the front surface of the liquid crystal light blocking section, thereby protecting the liquid crystal member from sputters and mechanical stress during the welding operation.

3. The welding-operation, liquid crystal, protection mask of claim 1, wherein the polarizing member is a polarizing film.

4. The welding-operation, liquid crystal, protection mask of claim 1, wherein the polarizing member is so constructed that when lights are incident on the polarizing member, only the lights having incidence angles of 24 degrees or smaller are allowed to pass through the polarizing member, thereby effecting the control of the orientation or the incident arc light.

5. The welding-operation, liquid crystal, protection mask of claim 1, wherein the detecting means includes an open-ended cylindrical member disposed in a predetermined position adjacent to the liquid crystal light blocking section, and a light receiving member disposed on the bottom of the open-ended cylindrical member for receiving an incident light.

6. The welding-operation, liquid crystal, protection mask of claim 1, wherein the liquid crystal member is a liquid crystal plate.

7. The welding-operation, liquid crystal, protection mask of claim 1, wherein the liquid crystal driving power source is a solar battery.

8. The welding-operation, liquid crystal, protection mask of claim 2, wherein the cover plate is a transparent protection plate.

9. The welding operation liquid crystal protection mask of claim 1, wherein the polarizing member allows light to pass therethrough to enable the detector to produce a detection result when the light is incident thereon at an angle of 24° or less.

10. A welding-operation protection mask that comprises:
   (a) a mask main body;
   (b) a liquid crystal unit disposed on the main body and comprising a liquid crystal light blocking section for reducing light transmittance to protect the eyes of a wearer;
   (c) a light detector that is capable of detecting light generated during a welding procedure, the light detector generating a signal that results in having the liquid crystal light blocking section reduce light transmittance; and
   (d) a polarizing member that is disposed in a position such that welding light incident upon the light detector will first pass through the polarizing member, the polarizing member allowing incident light to pass therethrough to cause the detector to produce a detection result when the incident light strikes the detection normal thereto but which polarizing member blocks the same incident light sufficiently to prevent the detector from producing a detection result when the light is incident thereon at a certain angle greater than a normal angle of incidence.

11. The welding-operation protection mask of claim 10, wherein the polarizing member is a polarizing film.

12. The welding operation liquid crystal protection mask of claim 10, wherein the polarizing member allows light to pass therethrough to enable the detector to produce a detection result when the light is incident thereon at an angle of 24° or less.

* * * * *